(12) United States Patent
Schnorr et al.

(10) Patent No.: US 7,972,814 B2
(45) Date of Patent: *Jul. 5, 2011

(54) **ANTIMICROBIAL POLYPEPTIDES FROM *PSEUDOPLECTANIA NIGRELLA***

(75) Inventors: Kirk Matthew Schnorr, Holte (DK); Mogens Trier Hansen, Soborg (DK); Per Holse Mygind, Soborg (DK); Dorotea Raventos Segura, Humlebaek (DK); Hans-Henrik Hogenhaug Kristensen, Holte (DK)

(73) Assignee: Novozymes Adenivro Biotech A/S

( * ) Notice: Subject to any disclaimer, the term of this patent is extended or adjusted under 35 U.S.C. 154(b) by 913 days.

This patent is subject to a terminal disclaimer.

(21) Appl. No.: 10/496,229

(22) PCT Filed: Nov. 20, 2002

(86) PCT No.: PCT/DK02/00781
§ 371 (c)(1), (2), (4) Date: May 18, 2004

(87) PCT Pub. No.: WO03/044049
PCT Pub. Date: May 30, 2003

(65) Prior Publication Data
US 2005/0124064 A1   Jun. 9, 2005

Related U.S. Application Data

(60) Provisional application No. 60/333,316, filed on Nov. 26, 2001, provisional application No. 60/407,120, filed on Aug. 30, 2002.

(30) Foreign Application Priority Data

Nov. 20, 2001 (DK) ................................. 2001 01732
Aug. 23, 2002 (DK) ................................. 2002 01243

(51) Int. Cl.
A61K 8/00 (2006.01)
A61K 39/00 (2006.01)
C12P 21/04 (2006.01)
C12P 21/06 (2006.01)

(52) U.S. Cl. .................. 435/71.1; 424/70.21; 424/185.1; 426/807; 435/69.1; 435/822

(58) Field of Classification Search .................. None
See application file for complete search history.

(56) References Cited

U.S. PATENT DOCUMENTS 6,448,056 B1 * 9/2002 Nielsen ......................... 435/193
6,482,799 B1 * 11/2002 Tuse et al. ...................... 514/14

FOREIGN PATENT DOCUMENTS

| EP | 1 146 052 | 10/2001 |
| WO | WO 98/38288 | 9/1998 |
| WO | WO99/53053 | * 10/1999 |
| WO | WO 00/73433 | 12/2000 |

OTHER PUBLICATIONS

Suay et al., SAntonie van Leeuwenhoek, vol. 78, No. 2, pp. 129-139 (2000).
Chmiel et al., Biuletyn Lubelskiego Towarzystwa Nuakowiego Biologia, vol. 28, No. 1, pp. 3-10 (1986) (abstract).
Nakajima, Database SWALL, Acces. No. Q9BLJ3 (2001).
Presnail et al., Database GSN, Acces. No. AAH77210 (2002).

* cited by examiner

*Primary Examiner* — Deborah K. Ware
(74) *Attorney, Agent, or Firm* — Elias Lanbiris

(57) ABSTRACT

The present invention relates to polypeptides having antimicrobial activity and polynucleotides having a nucleotide sequence which encodes for the polypeptides. The invention also relates to nucleic acid constructs, vectors, and host cells comprising the nucleic acid constructs as well as methods for producing and using the polypeptides.

15 Claims, No Drawings

ANTIMICROBIAL POLYPEPTIDES FROM *PSEUDOPLECTANIA NIGRELLA*

CROSS-REFERENCE TO RELATED APPLICATIONS

This application is a 35 U.S.C. 371 national application of PCT/DK02/00781 filed Nov. 20, 2002, which claims priority or the benefit under 35 U.S.C. 119 of Danish application nos. PA 2001 01732, filed Nov. 20, 2001, and PA 2002 01243, filed Aug. 23, 2002 and U.S. provisional application Nos. 60/333,316, filed Nov. 26, 2001, and 60/407,120, filed Aug. 30, 2002, the contents of which are fully incorporated herein by reference.

FIELD OF THE INVENTION

The present invention relates to polypeptides having antimicrobial activity and polynucleotides having a nucleotide sequence which encodes for the polypeptides. The invention also relates to nucleic acid constructs, vectors, and host cells comprising the nucleic acid constructs as well as methods for producing and using the polypeptides.

BACKGROUND

It is an object of the present invention to provide polypeptides having antimicrobial activity and polynucleotides encoding the polypeptides.

SUMMARY

In a first aspect the present invention relates to a polypeptide having antimicrobial activity, selected from the group consisting of:
(a) a polypeptide comprising an amino acid sequence which has at least 65% identity with amino acids 1 to 40 of SEQ ID NO:2;
(b) a polypeptide comprising an amino acid sequence which has at least 65% identity with the polypeptide encoded by the antimicrobial polypeptide encoding part of the nucleotide sequence present in *Pseudoplectania nigrella* CBS 444.97;
(c) a polypeptide which is encoded by a nucleotide sequence which hybridizes under low stringency conditions with a polynucleotide probe selected from the group consisting of:
  (i) the complementary strand of nucleotides 166 to 285 of SEQ ID NO:1,
  (ii) the complementary strand of nucleotides 70 to 285 of SEQ ID NO:1, and
  (iii) the complementary strand of nucleotides 1 to 285 of SEQ ID NO:1; and
(d) a fragment of (a), (b) or (c) that has antimicrobial activity.

In a second aspect the present invention relates to polynucleotides having a nucleotide sequence which encodes for the polypeptide of the invention.

In a third aspect the present invention relates to a nucleic acid construct comprising the nucleotide sequence, which encodes for the polypeptide of the invention, operably linked to one or more control sequences that direct the production of the polypeptide in a suitable host.

In a fourth aspect the present invention relates to a recombinant expression vector comprising the nucleic acid construct of the invention.

In a fifth aspect the present invention relates to a recombinant host cell comprising the nucleic acid construct of the invention.

In a sixth aspect the present invention relates to a method for producing a polypeptide of the invention, the method comprising:
(a) cultivating a strain, which in its wild-type form is capable of producing the polypeptide, to produce the polypeptide; and
(b) recovering the polypeptide.

In a seventh aspect the present invention relates to a method for producing a polypeptide of the invention, the method comprising:
(a) cultivating a recombinant host cell of the invention under conditions conducive for production of the polypeptide; and
(b) recovering the polypeptide.

Other aspects of the present invention will be apparent from the below description and from the appended claims.

DEFINITIONS

Prior to discussing the present invention in further details, the following terms and conventions will first be defined:

Substantially pure polypeptide: In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

Antimicrobial activity: The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect and/or a virucidal effect, wherein the term "bactericidal" is to be understood as capable of killing bacterial cells. The term "bacteriostatic" is to be understood as capable of inhibiting bacterial growth, i.e. inhibiting growing bacterial cells. The term "fungicidal" is to be understood as capable of killing fungal cells. The term "fungistatic" is to be understood as capable of inhibiting fungal growth, i.e. inhibiting growing fungal cells. The term "virucidal" is to be understood as capable of inactivating virus. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

For purposes of the present invention, antimicrobial activity may be determined according to the procedure described by Lehrer et al., Journal of Immunological Methods, Vol. 137 (2) pp. 167-174 (1991).

Polypeptides having antimicrobial activity may be capable of reducing the number of living cells of *Escherichia coli* (DSM 1576) to ¹/₁₀₀ after 30 min. incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Escherichia coli* (DSM 1576) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

Polypeptides having antimicrobial activity may be capable of reducing the number of living cells of *Bacillus subtilis* (ATCC 6633) to ¹/₁₀₀ after 30 min. incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The polypeptides of the present invention should preferably have at least 20% of the antimicrobial activity of the polypeptide consisting of the amino acid sequence shown as amino acids 1 to 40 of SEQ ID NO:2. In a particular preferred embodiment, the polypeptides should have at least 40%, such as at least 50%, preferably at least 60%, such as at least 70%, more preferably at least 80%, such as at least 90%, most preferably at least 95%, such as about or at least 100% of the antimicrobial activity of the polypeptide consisting of the amino acid sequence shown as amino acids 1 to 40 of SEQ ID NO:2.

Identity: In the present context, the homology between two amino acid sequences or between two nucleotide sequences is described by the parameter "identity".

For purposes of the present invention, the degree of identity between two amino acid sequences is determined by using the program FASTA included in version 2.0x of the FASTA program package (see W. R. Pearson and D. J. Lipman (1988), "Improved Tools for Biological Sequence Analysis", PNAS 85:2444-2448; and W. R. Pearson (1990) "Rapid and Sensitive Sequence Comparison with FASTP and FASTA", Methods in Enzymology 183:63-98). The scoring matrix used was BLOSUM50, gap penalty was −12, and gap extension penalty was −2.

The degree of identity between two nucleotide sequences is determined using the same algorithm and software package as described above. The scoring matrix used was the identity matrix, gap penalty was −16, and gap extension penalty was −4.

Fragment: When used herein, a "fragment" of SEQ ID NO:2 is a polypeptide having one or more amino acids deleted from the amino and/or carboxyl terminus of this amino acid sequence.

Allelic variant: In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems. Thus, a substantially pure polynucleotide contains at the most 10% by weight of other polynucleotide material with which it is natively associated (lower percentages of other polynucleotide material are preferred, e.g. at the most 8% by weight, at the most 6% by weight, at the most 5% by weight, at the most 4% at the most 3% by weight, at the most 2% by weight, at the most 1% by weight, and at the most %% by weight). A substantially pure polynucleotide may, however, include naturally occurring 5' and 3' untranslated regions, such as promoters and terminators. It is preferred that the substantially pure polynucleotide is at least 92% pure, i.e. that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99%, and at the most 99.5% pure. The polynucleotides disclosed herein are preferably in a substantially pure form. In particular, it is preferred that the polynucleotides disclosed herein are in "essentially pure form", i.e. that the polynucleotide preparation is essentially free of other polynucleotide material with which it is natively associated. Herein, the term "substantially pure polynucleotide" is synonymous with the terms "isolated polynucleotide" and "polynucleotide in isolated form".

Modification(s): In the context of the present invention the term "modification(s)" is intended to mean any chemical modification of the polypeptide consisting of the amino acid sequence shown as amino acids 1 to 40 of SEQ ID NO:2 as well as genetic manipulation of the DNA encoding that polypeptide. The modification(s) can be replacement(s) of the amino acid side chain(s), substitution(s), deletion(s) and/or insertions(s) in or at the amino acid(s) of interest.

Artificial variant: When used herein, the term "artificial variant" means a polypeptide having antimicrobial activity, which has been produced by an organism which is expressing a modified gene as compared to SEQ ID NO:1. The modified gene, from which said variant is produced when expressed in a suitable host, is obtained through human intervention by modification of the nucleotide sequence disclosed in SEQ ID NO:1.

cDNA: The term "cDNA" when used in the present context, is intended to cover a DNA molecule which can be prepared by reverse transcription from a mature, spliced, mRNA molecule derived from a eukaryotic cell. cDNA lacks the intron sequences that are usually present in the corresponding genomic DNA. The initial, primary RNA transcript is a precursor to mRNA and it goes through a series of processing events before appearing as mature spliced mRNA. These events include the removal of intron sequences by a process called splicing. When cDNA is derived from mRNA it therefore lacks intron sequences.

Nucleic acid construct: When used herein, the term "nucleic acid construct" means a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" is defined herein as a configuration in which a control sequence is appropriately placed at a position relative to the coding sequence of the DNA sequence such that the control sequence directs the expression of a polypeptide.

Coding sequence: When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically include DNA, cDNA, and recombinant nucleotide sequences.

Expression: In the present context, the term "expression" includes any step involved in the production of the polypeptide including, but not limited to, transcription, post-transcriptional modification, translation, post-translational modification, and secretion.

Expression vector: In the present context, the term "expression vector" covers a DNA molecule, linear or circular, that comprises a segment encoding a polypeptide of the invention, and which is operably linked to additional segments that provide for its transcription.

Host cell: The term "host cell", as used herein, includes any cell type which is susceptible to transformation with a nucleic acid construct.

The terms "polynucleotide probe", "hybridization" as well as the various stringency conditions are defined in the section entitled "Polypeptides Having Antimicrobial Activity".

DETAILED DESCRIPTION

Polypeptides Having Antimicrobial Activity

In a first embodiment, the present invention relates to polypeptides having antimicrobial activity and where the polypeptides comprises, preferably consists of, an amino acid sequence which has a degree of identity to amino acids 1 to 40 of SEQ ID NO:2 (i.e., the mature polypeptide) of at least 65%, preferably at least 70%, e.g. at least 75%, more preferably at least 80%, such as at least 85%, even more preferably at least 90%, most preferably at least 95%, e.g. at least 96%, such as at least 97%, and even most preferably at least 98%, such as at least 99% (hereinafter "homologous polypeptides"). In an interesting embodiment, the amino acid sequence differs by at the most ten amino acids (e.g. by ten amino acids), in particular by at the most five amino acids (e.g. by five amino acids), such as by at the most four amino acids (e.g. by four amino acids), e.g. by at the most three amino acids (e.g. by three amino acids) from amino acids 1 to 40 of SEQ ID NO:2. In a particular interesting embodiment, the amino acid sequence differs by at the most two amino acids (e.g. by two amino acids), such as by one amino acid from amino acids 1 to 40 of SEQ ID NO:2.

Preferably, the polypeptides of the present invention comprise the amino acid sequence of SEQ ID NO:2; an allelic variant thereof; or a fragment thereof that has antimicrobial activity. In another preferred embodiment, the polypeptide of the present invention comprises amino acids 1 to 40 of SEQ ID NO:2. In a further preferred embodiment, the polypeptide consists of amino acids 1 to 40 of SEQ ID NO:2.

The amino acids making up the polypeptide of the invention may independently be selected from D or L forms.

The polypeptide of the invention may be a wild-type polypeptide, having antimicrobial activity, identified and isolated from a natural source. Such wild-type polypeptides may be specifically screened for by standard techniques known in the art. Furthermore, the polypeptide of the invention may be prepared by the DNA shuffling technique, such as described in J. E. Ness et al. *Nature Biotechnology* 17, 893-896 (1999). Moreover, the polypeptide of the invention may be an artificial variant which comprises, preferably consists of, an amino acid sequence that has at least one substitution, deletion and/or insertion of an amino acid as compared to amino acids 1 to 40 of SEQ ID NO:2. Such artificial variants may be constructed by standard techniques known in the art, such as by site-directed/random mutagenesis of the polypeptide comprising the amino acid sequence shown as amino acids 1 to 40 of SEQ ID NO:2. In one embodiment of the invention, amino acid changes (in the artificial variant as well as in wild-type polypeptides) are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/ Arg, Asp/Asn, Leu/Ile, Leu/Val, Ala/Glu, and Asp/Gly as well as these in reverse.

In an interesting embodiment of the invention, the amino acid changes are of such a nature that the physico-chemical properties of the polypeptides are altered. For example, amino acid changes may be performed, which improve the thermal stability of the polypeptide, which alter the substrate specificity, which changes the pH optimum, and the like.

Preferably, the number of such substitutions, deletions and/ or insertions as compared to amino acids 1 to 40 of SEQ ID NO:2 is at the most 10, such as at the most 9, e.g. at the most 8, more preferably at the most 7, e.g. at the most 6, such as at the most 5, most preferably at the most 4, e.g. at the most 3, such as at the most 2, in particular at the most 1.

The present inventors have isolated a gene encoding a polypeptide having antimicrobial activity from *Pseudoplectania nigrella*. The *Pseudoplectania nigrella* strain harboring the gene was deposited according to the Budapest Treaty on the International Recognition of the Deposits of Microorganisms for the Purpose of Patent Procedures on 28 Jan. 1997 at the Centraalbureau Voor Schimmelcultures (CBS), Uppsalalaan 8, 3584 CT Utrecht, The Netherlands (alternatively P.O. Box 85167, 3508 AD Utrecht, The Netherlands), and designated the accession No. CBS 444.97.

Thus, in a second embodiment, the present invention relates to polypeptides comprising, preferably consisting of, an amino acid sequence which has at least 65% identity with the antimicrobial polypeptide encoding part of the nucleotide sequence present in *Pseudoplectania nigrella* CBS 444.97. In an interesting embodiment of the invention, the polypeptide comprises, preferably consists of, an amino acid sequence which has at least 70%, e.g. at least 75%, preferably at least 80%, such as at least 85%, more preferably at least 90%, most preferably at least 95%, e.g. at least 96%, such as at least 97%, and even most preferably at least 98%, such as at least 99% identity with the antimicrobial polypeptide encoding part of the nucleotide sequence present in *Pseudoplectania nigrella* CBS 444.97 (hereinafter "homologous polypeptides"). In an interesting embodiment, the amino acid sequence differs by at the most ten amino acids (e.g. by ten amino acids), in particular by at the most five amino acids (e.g. by five amino acids), such as by at the most four amino acids (e.g. by four amino acids), e.g. by at the most three amino acids (e.g. by three amino acids) from the antimicrobial polypeptide encoding part of the nucleotide sequence present in *Pseudoplectania nigrella* CBS 444.97. In a particular interesting embodiment, the amino acid sequence differs by at the most two amino acids (e.g. by two amino acids), such as by one amino acid from the antimicrobial polypeptide encoding part of the nucleotide sequence present in *Pseudoplectania nigrella* CBS 444.97.

Preferably, the polypeptides of the present invention comprise the amino acid sequence of the antimicrobial polypeptide encoding part of the nucleotide sequence present in *Pseudoplectania nigrella* CBS 444.97. In another preferred embodiment, the polypeptide of the present invention consists of the amino acid sequence of the polypeptide encoded by the antimicrobial polypeptide encoding part of the nucleotide sequence present in *Pseudoplectania nigrella* CBS 444.97.

In a similar way as described above, the polypeptide of the invention may be an artificial variant which comprises, preferably consists of, an amino acid sequence that has at least one substitution, deletion and/or insertion of an amino acid as compared to the amino acid sequence encoded by the antimicrobial polypeptide encoding part of the nucleotide sequence present in *Pseudoplectania nigrella* CBS 444.97.

In a third embodiment, the present invention relates to polypeptides having antimicrobial activity which are encoded by nucleotide sequences which hybridize under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe selected from the group consisting of (i) the complementary strand of nucleotides 166 to 285 of SEQ ID NO:1, (ii) the complementary strand of the cDNA sequence contained in nucleotides 70 to 285 of SEQ ID NO:1, and (iii) the complementary strand of nucleotides 1 to 285 of SEQ ID NO:1 (J. Sambrook, E. F. Fritsch, and T. Maniatus, 1989, *Molecular Cloning, A Laboratory Manual*, 2d edition, Cold Spring Harbor, N.Y.).

The nucleotide sequence of SEQ ID NO:1 or a subsequence thereof, as well as the amino acid sequence of SEQ ID NO:2 or a fragment thereof, may be used to design a polynucleotide probe to identify and clone DNA encoding polypeptides having antimicrobial activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, more preferably at least 35 nucleotides in length, such as at least 70 nucleotides in length. It is, however, preferred that the polynucleotide probe is at least 100 nucleotides in length. For example, the polynucleotide probe may be at least 200 nucleotides in length, at least 300 nucleotides in length, at least 400 nucleotides in length or at least 500 nucleotides in length. Even longer probes may be used, e.g., polynucleotide probes which are at least 600 nucleotides in length, at least 700 nucleotides in length, at least 800 nucleotides in length, or at least 900 nucleotides in length. Both DNA and RNA probes can be used. The probes are typically labeled for detecting the corresponding gene (for example, with $^{32}$P, $^{3}$H, $^{35}$S, biotin, or avidin).

Thus, a genomic DNA or cDNA library prepared from such other organisms may be screened for DNA which hybridizes with the probes described above and which encodes a polypeptide having antimicrobial activity. Genomic or other DNA from such other organisms may be separated by agarose or polyacrylamide gel electrophoresis, or other separation techniques. DNA from the libraries or the separated DNA may be transferred to, and immobilized, on nitrocellulose or other suitable carrier materials. In order to identify a clone or DNA which is homologous with SEQ ID NO:1 the carrier material with the immobilized DNA is used in a Southern blot.

For purposes of the present invention, hybridization indicates that the nucleotide sequence hybridizes to a labeled polynucleotide probe which hybridizes to the nucleotide sequence shown in SEQ ID NO:1 under very low to very high stringency conditions. Molecules to which the polynucleotide probe hybridizes under these conditions may be detected using X-ray film or by any other method known in the art. Whenever the term "polynucleotide probe" is used in the present context, it is to be understood that such a probe contains at least 15 nucleotides.

In an interesting embodiment, the polynucleotide probe is the complementary strand of nucleotides 166 to 285, nucleotides 70 to 285, or nucleotides 1 to 285 of SEQ ID NO:1.

In another interesting embodiment, the polynucleotide probe is the complementary strand of the nucleotide sequence which encodes the polypeptide of SEQ ID NO:2. In a further interesting embodiment, the polynucleotide probe is the complementary strand of SEQ ID NO:1. In a still further interesting embodiment, the polynucleotide probe is the complementary strand of the mature polypeptide coding region of SEQ ID NO:1. In another interesting embodiment, the polynucleotide probe is the complementary strand of the antimicrobial polypeptide encoding region present in *Pseudoplectania nigrella* CBS 444.97. In still another interesting embodiment, the polynucleotide probe is the complementary strand of the mature antimicrobial polypeptide encoding region present in *Pseudoplectania nigrella* CBS 444.97.

For long probes of at least 100 nucleotides in length, very low to very high stringency conditions are defined as prehybridization and hybridization at 42° C. in 5×SSPE, 1.0% SDS, 5×Denhardt's solution, 100 μg/ml sheared and denatured salmon sperm DNA, following standard Southern blotting procedures. Preferably, the long probes of at least 100 nucleotides do not contain more than 1000 nucleotides. For long probes of at least 100 nucleotides in length, the carrier material is finally washed three times each for 15 minutes using 2×SSC, 0.1% SDS at 42° C. (very low stringency), preferably washed three times each for 15 minutes using 0.5×SSC, 0.1% SDS at 42° C. (low stringency), more preferably washed three times each for 15 minutes using 0.2×SSC, 0.1% SDS at 42° C. (medium stringency), even more preferably washed three times each for 15 minutes using 0.2×SSC, 0.1% SDS at 55° C. (medium-high stringency), most preferably washed three times each for 15 minutes using 0.1×SSC, 0.1% SDS at 60° C. (high stringency), in particular washed three times each for 15 minutes using 0.1×SSC, 0.1% SDS at 68° C. (very high stringency).

Although not particularly preferred, it is contemplated that shorter probes, e.g. probes which are from about 15 to 99 nucleotides in length, such as from about 15 to about 70 nucleotides in length, may be also be used. For such short probes, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to 99 nucleotides in length, the carrier material is washed once in 6×SCC plus 0.1% SDS for 15 minutes and twice each for 15 minutes using 6×SSC at 5° C. to 10° C. below the calculated $T_m$.

N-Terminal Extension

A N-terminal extension may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as a N-terminal extension comprising one of the following sequences: EAE, EE, DE, DD.

Kex2 Sites

Kex2 sites (see, e.g., Methods in Enzymology Vol 185, ed. D. Goeddel, Academic Press Inc. (1990), San Diego, Calif., "Gene Expression Technology") and kex2-like sites are dibasic recognition sites (i.e., cleavage sites) found between the pro-peptide encoding region and the mature region of some proteins.

Insertion of a kex2 site or a kex2-like site have in certain cases been shown to improve correct endopeptidase processing at the pro-peptide cleavage site resulting in increased protein secretion levels.

In the context of the invention insertion of a kex2 or kex2-like site result in the possibility to obtain cleavage at a certain position in the N-terminal extension resulting in an antimicrobial polypeptide being extended in comparison to the mature polypeptide shown as amino acids 1 to 40 of SEQ ID NO:2.

Sources for Polypeptides Having Antimicrobial Activity

A polypeptide of the present invention may be obtained from microorganisms of any genus. For purposes of the present invention, the term "obtained from" as used herein shall mean that the polypeptide encoded by the nucleotide sequence is produced by a cell in which the nucleotide sequence is naturally present or into which the nucleotide sequence has been inserted. In a preferred embodiment, the polypeptide is secreted extracellularly.

A polypeptide of the present invention may be a bacterial polypeptide. For example, the polypeptide may be a gram positive bacterial polypeptide such as a *Bacillus* polypeptide, e.g., a *Bacillus alkatophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a *Candida, Kluyveromyces, Pichia, Saccharomyces, Schizosaccharomyces,* or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* polypeptide.

In an interesting embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another interesting embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicil-*

*lium purpurogenum, Trichoderma harzianum, Trichoderma koningii, Trichoderma longibrachiatum, Trichoderma reesei,* or *Trichoderma viride* polypeptide.

In a preferred embodiment, the polypeptide is a *Pseudoplectania nigrella* polypeptide, and more preferably a *Pseudoplectania nigrella* CBS 444.97 polypeptide, e.g., the polypeptide consisting of the amino acid sequence 1 to 40 of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleotide sequence may then be derived by similarly screening a genomic or cDNA library of another microorganism. Once a nucleotide sequence encoding a polypeptide has been detected with the probe(s), the sequence may be isolated or cloned by utilizing techniques which are known to those of ordinary skill in the art (see, e.g., Sambrook et al., 1989, supra).

Polypeptides encoded by nucleotide sequences of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides and Nucleotide Sequences

The present invention also relates to polynucleotides having a nucleotide sequence which encodes for a polypeptide of the invention. In particular, the present invention relates to polynucleotides consisting of a nucleotide sequence which encodes for a polypeptide of the invention. In a preferred embodiment, the nucleotide sequence is set forth in SEQ ID NO:1. In a more preferred embodiment, the nucleotide sequence is the mature polypeptide coding region of SEQ ID NO:1. In another more preferred embodiment, the nucleotide sequence is the mature antimicrobial polypeptide encoding region present in *Pseudoplectania nigrella* CBS 444.97. The present invention also encompasses polynucleotides having, preferably consisting of, nucleotide sequences which encode a polypeptide consisting of the amino acid sequence of SEQ ID NO:2 or the mature polypeptide thereof, which differ from SEQ ID NO:1 by virtue of the degeneracy of the genetic code.

The present invention also relates to polynucleotides having, preferably consisting of, a subsequence of SEQ ID NO:1 which encode fragments of SEQ ID NO:2 that have antimicrobial activity. A subsequence of SEQ ID NO:1 is a nucleotide sequence encompassed by SEQ ID NO:1 except that one or more nucleotides from the 5' and/or 3' end have been deleted.

The present invention also relates to polynucleotides having, preferably consisting of, a modified nucleotide sequence which comprises at least one modification in the mature polypeptide coding sequence of SEQ ID NO:1, and where the modified nucleotide sequence encodes a polypeptide which consists of amino acids 1 to 40 of SEQ ID NO:2.

The techniques used to isolate or clone a nucleotide sequence encoding a polypeptide are known in the art and include isolation from genomic DNA, preparation from cDNA, or a combination thereof. The cloning of the nucleotide sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other amplification procedures such as ligase chain reaction (LCR), ligated activated transcription (LAT) and nucleotide sequence-based amplification (NASBA) may be used. The nucleotide sequence may be cloned from a strain of antimicrobial polypeptide encoding nucleotide sequence present in *Pseudoplectania*, or another or related organism and thus, for example, may be an allelic or species variant of the polypeptide encoding region of the nucleotide sequence.

The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

The present invention also relates to a polynucleotide having, preferably consisting of, a nucleotide sequence which has at least 65% identity with nucleotides 166 to 285 of SEQ ID NO:1. Preferably, the nucleotide sequence has at least 70% identity, e.g. at least 80% identity, such as at least 90% identity, more preferably at least 95% identity, such as at least 96% identity, e.g. at least 97% identity, even more preferably at least 98% identity, such as at least 99% with nucleotides 166 to 285 of SEQ ID NO:1. Preferably, the nucleotide sequence encodes a polypeptide having antimicrobial activity. The degree of identity between two nucleotide sequences is determined as described previously (see the section entitled "Definitions"). Preferably, the nucleotide sequence comprises nucleotides 166 to 285 of SEQ ID NO:1. In an even more preferred embodiment, the nucleotide sequence consists of nucleotides 166 to 285 of SEQ ID NO:1.

In another interesting aspect, the present invention relates to a polynucleotide having, preferably consisting of, a nucleotide sequence which has at least 65% identity with the antimicrobial polypeptide encoding part of the nucleotide sequence present in antimicrobial polypeptide encoding nucleotide sequence present in *Pseudoplectania nigrella* CBS 444.97. In a preferred embodiment, the degree of identity with the antimicrobial polypeptide encoding part of the nucleotide sequence present in antimicrobial polypeptide encoding nucleotide sequence present in *Pseudoplectania nigrella* CBS 444.97 is at least 70%, e.g. at least 80%, such as at least 90%, more preferably at least 95%, such as at least 96%, e.g. at least 97%, even more preferably at least 98%, such as at least 99%. Preferably, the nucleotide sequence comprises the antimicrobial encoding part of the nucleotide sequence present in antimicrobial polypeptide encoding nucleotide sequence present in *Pseudoplectania nigrella* CBS 444.97. In an even more preferred embodiment, the nucleotide sequence consists of the antimicrobial polypeptide encoding part of the nucleotide sequence present in antimicrobial polypeptide encoding nucleotide sequence present in *Pseudoplectania nigrella* CBS 444.97.

Modification of a nucleotide sequence encoding a polypeptide of the present invention may be necessary for the synthesis of a polypeptide, which comprises an amino acid sequence that has at least one substitution, deletion and/or insertion as compared to amino acids 1 to 40 of SEQ ID NO:2. These artificial variants may differ in some engineered way from the polypeptide isolated from its native source, e.g., variants that differ in specific activity, thermostability, pH optimum, or the like.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for antimicrobial activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitution, see, e.g., Ford et al., 1991, *Protein Expression and Purification* 2: 95-107.

The present invention also relates to a polynucleotide having, preferably consisting of, a nucleotide sequence which encodes a polypeptide having antimicrobial activity, and which hybridizes under very low stringency conditions, preferably under low stringency conditions, more preferably under medium stringency conditions, more preferably under medium-high stringency conditions, even more preferably under high stringency conditions, and most preferably under very high stringency conditions with a polynucleotide probe selected from the group consisting of (i) the complementary strand of nucleotides 166 to 285 of SEQ ID NO:1, (ii) the complementary strand of the cDNA sequence contained in nucleotides 70 to 285 of SEQ ID NO:1, and (iii) the complementary strand of nucleotides 1 to 285 of SEQ ID NO:1.

As will be understood, details and particulars concerning hybridization of the nucleotide sequences will be the same or analogous to the hybridization aspects discussed in the section entitled "Polypeptides Having Antimicrobial Activity" herein.

Nucleic Acid Constructs

The present invention also relates to nucleic acid constructs comprising a nucleotide sequence of the present invention operably linked to one or more control sequences that direct the expression of the coding sequence in a suitable host cell under conditions compatible with the control sequences.

A nucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

The signal peptide coding region is nucleotides 1 to 69 of SEQ ID NO:1 which encode amino acids −55 to −33 of SEQ ID NO:2 (or amino acids 1 to 23 of SEQ ID NO:3).

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57:109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

The propeptide coding region is nucleotides 70 to 165 of SEQ ID NO:1 which encode amino acids −32 to −1 of SEQ ID NO:2 (or amino acids 24 to 55 of SEQ ID NO:3).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising the nucleic acid construct of the invention. The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus,* or gram negative bacteria such as *E. coli* and *Pseudomonas* sp. In a preferred embodiment, the bacterial host cell is a *Bacillus lentus, Bacillus licheniformis, Bacillus stearothermophilus,* or *Bacillus subtilis* cell. In another preferred embodiment, the *Bacillus* cell is an alkalophilic *Bacillus.*

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma.*

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (*Nirenberg* sp. *nov.*) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide; and (b) recovering the polypeptide. Preferably, the strain is of the genus *Pseudoplectania,* and more preferably *Pseudoplectania nigrella.*

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having antimicrobial activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor. The recovered polypeptide, plant or plant part may also be used to improve or alter digestive flora in animals and livestock.

The transgenic plant can be dicotyledonous (a dicot) or monocotyledonous (a monocot). Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, potato, sugar beet, legumes, such as lupins, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleotide sequence encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleotide sequence encoding a polypeptide having antimicrobial activity of the present invention under conditions conducive for production of the polypeptide; and (b) recovering the polypeptide.

Compositions

In a still further aspect, the present invention relates to compositions, such as pharmaceutical compositions, comprising an antimicrobial polypeptide of the invention.

The composition may comprise a polypeptide of the invention as the major polypeptide component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenyloxidase, proteolytic enzyme, ribonuclease, transglutaminase, or xylanase.

The compositions may further comprise another pharmaceutically active agent, such as an additional biocidal agent, such as another antimicrobial polypeptide exhibiting antimicrobial activity as defined above. The biocidal agent may be an antibiotic, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. The biocidal agent may also be an anti-mycotic agent, including polyenes, e.g. amphotericin B, nystatin; 5-flucosyn; and azoles, e.g. miconazol, ketoconazol, itraconazol and fluconazol.

In an embodiment the biocidal agent is a non-enzymatic chemical agent. In another embodiment the biocidal agent is a non-polypeptide chemical agent.

The biocidal agent may be capable of reducing the number of living cells of *Escherichia coli* (DSM 1576) to $\frac{1}{100}$ after 30 min. incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the biocidal agent.

The biocidal agent may also be capable of inhibiting the outgrowth of *Escherichia coli* (DSM 1576) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The biocidal agent may also be capable of reducing the number of living cells of *Bacillus subtilis* (ATCC 6633) to $\frac{1}{100}$ after 30 min. incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the biocidal agent.

The biocidal agent may also be capable of inhibiting the outgrowth of *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The antimicrobial polypeptide of the invention and the biocidal agent of the composition may be selected so that a synergistic antimicrobial effect is obtained.

The antimicrobial polypeptide and the biocidal agent of the composition may be selected so that the number of living cells of *E. coli* (DSM 1576), when incubated 10 min. at 20° C. in an aqueous solution containing 50% w/w (preferably 25% w/w, more preferably 10% w/w, most preferably 5% w/w) of the biocidal agent and 0.5 ppm (preferably 0.1 ppm) of the antimicrobial polypeptide, are reduced at least 5% (preferably at least 10%) more than compared to what is obtained by adding the results of separate incubations with the biocidal agent and the antimicrobial polypeptide alone, i.e. a simple additive effect.

The enzymatic component and the biocidal agent of the composition may also be selected so that the outgrowth of *E. coli* (DSM 1576) at 25° C. in a microbial growth substrate containing 500 ppm (preferably 250 ppm, more preferably 100 ppm, most preferably 50 ppm) of the biocidal agent and 0.5 ppm (preferably 0.1 ppm) of the antimicrobial polypeptide, are inhibited at least 5% (preferably at least 10%) longer time than compared to what is obtained by adding the results of separate incubations with the biocidal agent and the antimicrobial polypeptide alone, i.e. a simple additive effect.

The antimicrobial polypeptide and the biocidal agent of the composition may also be selected so that the number of living cells of *Bacillus subtilis* (ATCC 6633), when incubated 10 min. at 20° C. in an aqueous solution containing 50% w/w (preferably 25% w/w, more preferably 10% w/w, most preferably 5% w/w) of the biocidal agent and 0.5 ppm (preferably 0.1 ppm) of the antimicrobial polypeptide, are reduced at least 5% (preferably at least 10%) more than compared to what is obtained by adding the results of separate incubations with the biocidal agent and the antimicrobial polypeptide alone, i.e. a simple additive effect.

The enzymatic component and the biocidal agent of the composition may also be selected so that the outgrowth of *Bacillus subtilis* (ATCC 6633) at 25° C. in a microbial growth substrate containing 500 ppm (preferably 250 ppm, more preferably 100 ppm, most preferably 50 ppm) of the biocidal agent and 0.5 ppm (preferably 0.1 ppm) of the antimicrobial polypeptide, are inhibited at least 5% (preferably at least 10%) longer time than compared to what is obtained by adding the results of separate incubations with the biocidal agent and the antimicrobial polypeptide alone, i.e. a simple additive effect.

The compositions may comprise a suitable carrier material. The compositions may also comprise a suitable delivery vehicle capable of delivering the antimicrobial polypeptides of the invention to the desired locus when the compositions are used as a medicament.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Methods and Uses

The present invention also encompasses various uses of antimicrobial polypeptides. The antimicrobial polypeptides are typically useful at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, the present invention may also be used in all applications for which known antimicrobial compositions are useful, such as protection of wood, latex, adhesive, glue, paper, cardboard, textile, leather, plastics, caulking, and feed.

Other uses include preservation of foods, beverages, cosmetics such as lotions, creams, gels, ointments, soaps, shampoos, conditioners, antiperspirants, deodorants, mouth wash, contact lens products, enzyme formulations, or food ingredients.

Thus, the antimicrobial polypeptides of the invention may by useful as a disinfectant, e.g., in the treatment of acne, infections in the eye or the mouth, skin infections; in antiperspirants or deodorants; in foot bath salts; for cleaning and disinfection of contact lenses, hard surfaces, teeth (oral care), wounds, bruises and the like.

In general it is contemplated that the antimicrobial polypeptides of the present invention are useful for cleaning, disinfecting or inhibiting microbial growth on any hard surface. Examples of surfaces, which may advantageously be contacted with the antimicrobial polypeptides of the invention are surfaces of process equipment used e.g. dairies, chemical or pharmaceutical process plants, water sanitation systems, oil processing plants, paper pulp processing plants, water treatment plants, and cooling towers. The antimicrobial polypeptides of the invention should be used in an amount, which is effective for cleaning, disinfecting or inhibiting microbial growth on the surface in question.

Further, it is contemplated that the antimicrobial polypeptides of the invention can advantageously be used in a cleaning-in-place (C.I.P.) system for cleaning of process equipment of any kind.

The antimicrobial polypeptides of the invention may additionally be used for cleaning surfaces and cooking utensils in food processing plants and in any area in which food is prepared or served such as hospitals, nursing homes, restaurants, especially fast food restaurants, delicatessens and the like. It may be used as an antimicrobial in food products and would also be especially useful as a surface antimicrobial in cheeses, fruits and vegetables and food on salad bars.

It may also be used as a preservation agent or a disinfection agent in water based paints.

The antimicrobial polypeptides of the present invention are also useful for microbial control of water lines, and for disinfection of water, in particular for disinfection of industrial water.

The invention also relates to the use of an antimicrobial polypeptide or composition of the invention as a medicament. Further, an antimicrobial polypeptide or composition of the invention may also be used for the manufacture of a medicament for controlling or combating microorganisms, such as fungal organisms or bacteria, preferably gram positive bacteria.

The composition and antimicrobial polypeptide of the invention may be used as an antimicrobial veterinarian or human therapeutic or prophylactic agent. Thus, the composition and antimicrobial polypeptide of the invention may be used in the preparation of veterinarian or human therapeutic agents or prophylactic agents for the treatment of microbial infections, such as bacterial or fungal infections, preferably gram positive bacterial infections. In particular the microbial infections may be associated with lung diseases including, but not limited to, tuberculosis and cystic fibrosis; and sexual transmitted diseases including, but not limited to, gonorrhea and chlamydia.

The composition of the invention comprises an effective amount of the antimicrobial polypeptide of the invention.

The term "effective amount" when used herein is intended to mean an amount of the antimicrobial polypeptide comprising the amino acid sequence shown as amino acids 1 to 40 of SEQ ID NO:2, or a fragment or a variant thereof, which is sufficient to inhibit growth of the microorganisms in question.

The invention also relates to wound healing compositions or products such as bandages, medical devices such as, e.g., catheters and further to anti-dandruff hair products, such as shampoos.

In Vitro Synthesis

The antimicrobial peptides of the invention may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Animal Feed

The present invention is also directed to methods for using the polypeptides having antimicrobial activity in animal feed, as well as to feed compositions and feed additives comprising the antimicrobial polypeptides of the invention.

The term animal includes all animals, including human beings. Examples of animals are non-ruminants, and ruminants, such as cows, sheep and horses. In a particular embodiment, the animal is a non-ruminant animal. Non-ruminant animals include mono-gastric animals, e.g. pigs or swine (including, but not limited to, piglets, growing pigs, and sows); poultry such as turkeys and chicken (including but not limited to broiler chicks, layers); young calves; and fish (including but not limited to salmon).

The term feed or feed composition means any compound, preparation, mixture, or composition suitable for, or intended for intake by an animal.

In the use according to the invention the antimicrobial polypeptide can be fed to the animal before, after, or simultaneously with the diet. The latter is preferred.

In a particular embodiment, the antimicrobial polypeptide, in the form in which it is added to the feed, or when being included in a feed additive, is well defined. Well-defined means that the antimicrobial polypeptide preparation is at least 50% pure as determined by Size-exclusion chromatography (see Example 12 of WO 01/58275). In other particular embodiments the antimicrobial polypeptide preparation is at least 60, 70, 80, 85, 88, 90, 92, 94, or at least 95% pure as determined by this method.

A well-defined antimicrobial polypeptide preparation is advantageous. For instance, it is much easier to dose correctly to the feed an antimicrobial polypeptide that is essentially free from interfering or contaminating other antimicrobial polypeptides. The term dose correctly refers in particular to the objective of obtaining consistent and constant results, and the capability of optimising dosage based upon the desired effect.

For the use in animal feed, however, the antimicrobial polypeptide need not be that pure; it may e.g. include other enzymes, in which case it could be termed an antimicrobial polypeptide preparation.

The antimicrobial polypeptide preparation can be (a) added directly to the feed (or used directly in a treatment process of vegetable proteins), or (b) it can be used in the production of one or more intermediate compositions such as feed additives or premixes that is subsequently added to the feed (or used in a treatment process). The degree of purity described above refers to the purity of the original antimicrobial polypeptide preparation, whether used according to (a) or (b) above.

Antimicrobial polypeptide preparations with purities of this order of magnitude are in particular obtainable using recombinant methods of production, whereas they are not so easily obtained and also subject to a much higher batch-to-batch variation when the antimicrobial polypeptide is produced by traditional fermentation methods.

Such antimicrobial polypeptide preparation may of course be mixed with other enzymes.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

The antimicrobial polypeptide can be added to the feed in any form, be it as a relatively pure antimicrobial polypeptide, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the antimicrobial polypeptide of the invention, the animal feed additives of the invention contain at least one fat soluble vitamin, and/or at least one water soluble vitamin, and/or at least one trace mineral, and/or at least one macro mineral.

Further, optional, feed-additive ingredients are colouring agents, aroma compounds, stabilisers, and/or at least one other enzyme selected from amongst phytases EC 3.1.3.8 or 3.1.3.26; xylanases EC 3.2.1.8; galactanases EC 3.2.1.89; and/or beta-glucanases EC 3.2.1.4.

In a particular embodiment these other enzymes are well defined (as defined above for antimicrobial polypeptide preparations).

Examples of other antimicrobial peptides (AMP's) are CAP18, Leucocin A, Tritrpticin, Protegrin-1, Thanatin, Defensin, Ovispirin such as Novispirin (Robert Lehrer, 2000), and variants, or fragments thereof which retain antimicrobial activity.

Examples of other antifungal polypeptides (AFP's) are the *Aspergillus giganteus*, and *Aspergillus niger* peptides, as well as variants and fragments thereof which retain antifungal activity, as disclosed in WO 94/01459 and PCT/DK02/00289 [replace with WO number once published].

Usually fat and water soluble vitamins, as well as trace minerals form part of a so-called premix intended for addition to the feed, whereas macro minerals are usually separately added to the feed. Either of these composition types, when enriched with an antimicrobial polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat soluble vitamins are vitamin A, vitamin D3, vitamin E, and vitamin K, e.g. vitamin K3.

Examples of water soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one antimicrobial polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 D A Beekbergen, The Netherlands. Grafisch bedrijf Ponsen & Iooijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey. Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 5-30 mg enzyme protein per kg animal diet.

The antimicrobial polypeptide may be administered in one or more of the following amounts (dosage ranges): 0.01-200; or 0.01-100; or 0.05-100; or 0.05-50; or 0.10-10—all these ranges being in mg antimicrobial polypeptide protein per kg feed (ppm).

For determining mg antimicrobial polypeptide protein per kg feed, the antimicrobial polypeptide is purified from the feed composition, and the specific activity of the purified antimicrobial polypeptide is determined using a relevant assay (see under antimicrobial activity, substrates, and assays). The antimicrobial activity of the feed composition as such is also determined using the same assay, and on the basis of these two determinations, the dosage in mg antimicrobial polypeptide protein per kg feed is calculated.

The same principles apply for determining mg antimicrobial polypeptide protein in feed additives. Of course, if a sample is available of the antimicrobial polypeptide used for preparing the feed additive or the feed, the specific activity is determined from this sample (no need to purify the antimicrobial polypeptide from the feed composition or the additive).

Detergent Composition

The antimicrobial polypeptides of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the antimicrobial polypeptides of the invention and a surfactant. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase (such as a laccase), and/or a peroxidase (such as a haloperoxidase).

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas lipase*, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus lipase*, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenyls having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenyl ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, and the antimicrobial polypeptides of the invention, may be added in an amount corresponding to 0.01-100 mg of enzyme protein per liter of wash liqour, preferably 0.05-10 mg of enzyme protein per liter of wash liqour, more preferably 0.1-5 mg of enzyme protein per liter of wash liqour, and most preferably 0.1-1 mg of enzyme protein per liter of wash liqour.

The antimicrobial polypeptides of the invention may additionally be incorporated in the detergent formulations disclosed in WO 97/07202 which is hereby incorporated as reference.

The present invention is further described by the following examples which should not be construed as limiting the scope of the invention.

EXAMPLES

Chemicals used as buffers and substrates were commercial products of at least reagent grade.

Example 1

Identification of an Antimicrobial Polypeptide from *Pseudoplectania nigrella*

Materials and Methods

A cDNA library was prepared from *P. nigrella* media induced for 5 days on Mex-1 media (protocol found in the examples of international patent application WO 98/38288). PolyA enriched RNA was purified, cDNA was synthesized and the library made according to standard molecular biology procedures. A detailed protocol on the general process can be found in the examples of international patent application WO 01/12794. Vector used for cloning was pMhas5, which is shown in SEQ ID NO:4 and has the following features:

TABLE 1

Features of vector pMhas5.

| Feature | Location | Description |
| --- | --- | --- |
| CDS | 365-1156 | Kanamycin resistance |
| CDS | 2232-2387 | Beta galactosidase alpha peptide |
| −10 signal | 2189-2192 | Shine Dalgarno |

TABLE 1-continued

Features of vector pMhas5.

| Feature | Location | Description |
| --- | --- | --- |
| promotor | 2101-2189 | Lac promotor |
| misc feature | 626-650 | KanP1 primer for BACE system |

Notable features of this plasmid are the EcoRI-NotI restriction sites proximal to the Shine Dalgarno region of the Lac promoter. This allows EcoRI-NotI adapted cDNAs to be cloned into the vector and the resulting constructs to be actively transcribed and translated in the *E. coli* host.

Construction of the *Pseudoplectania nigrella* Library and Signal Trapping of the cDNA Resulting Plasmid Pool A cDNA plasmid pool was prepared from 20,000 total transformants of the original cDNA-pMHas5 vector ligation. Plasmid DNA was prepared directly from a pool of colonies recovered from solid LB selective media according to the Qiagen protocol for plasmid DNA isolation (Qiagen Inc.). The plasmid pool was treated with transposon SigA2 and MuA transposase according to the transposase manufacturer's instructions (Finnizyme, Finland). General information about transposon assisted signal trapping can be found in international patent application WO 01/77315. The resulting mixture was ethanol precipitated to remove excess salt and 1.5 microliter electroporated into 20 microliter DH10B ultracompetent cells according to the standard protocol provided with the cells (Gibco-BRL). Electroporated cells were incubated in SOC media with shaking (28 degrees celcius, 2 hours, 250 rpm) before being plated on selective media. Three agar medias were used:

LB+50 microgram pr. ml kanamycin,
LB+kanamycin+15 microgram pr. ml chloramphencol, or
LB+kanamycin+chloramphenicol+12.5 microgram pr. ml ampicillin.

From dilution plating of the electroporation onto LB+kanamycin+chloramphenicol media, it was determined that approximately 119,000 colonies were present containing a cDNA library plasmid with a SigA2 transposition. In all 363 colonies were recovered from the experiment under triple selection. All 363 colonies were replica plated onto triple selection with 50 microgram pr. ml ampicillin to select for true signal trappants. A total of 336 colonies were able to grow under the increased ampicillin concentration and these were miniprepped according to the Qiagen Qiaturbo96 protocol (Qiagen Inc.). Plasmids were sequenced with the transposon forward and reverse primers (primers A and B) according to the procedure disclosed in the examples of international patent application WO 01/77315.

Primer A: agcgt ttgcg gccgc gatcc    (SEQ ID NO: 16)

Primer B: ttatt cggtc gaaaa ggatc    (SEQ ID NO: 17)
c

DNA sequence was obtained for the reactions on an AB3700 capillary sequencer. Sequences were trimmed to remove vector and transposon sequence and the A and B primer reads for each plasmid assembled. This resulted in 225 assembled sequences which were grouped by sequence homology into 145 contigs. All 145 contigs were independently blasted and the results analyzed. One plasmid (Plectasin_6_B12) shared some amino acid homology with known antimicrobial polypeptides (defensin-like polypeptides).

In the following examples the antimicrobial polypeptide of the invention is referred to as "Plectasin".

Example 2

Construction of an *Aspergillus* Expression Vector for Plectasin

The Plectasin encoding sequence was amplified from the above cDNA library (see Example 1 above) in the following manner: 1 microliter of cDNA (approximately 10 nanogram of DNA) was used as template in a PCR reaction with the two primers 178 and 179.

```
Primer 178: tctgg atcca ccatg caatt    (SEQ ID NO: 7)
            tacca ccatc ctctc Primer 179: tctct cgagc tagta acact    (SEQ ID NO: 8)
            tgcaa acaaa gc
```

10 pmole of each primer was used in a 100 microliter reaction volume. Annealing temperature was 55 degrees celcius, and extension at 72 degrees celcius for 1 minute. A total of 35 cycles were run. The Expand High Fidelity PCR System (Roche) was used.

Aliquots of the PCR reaction were separated on a 4% agarose gel. Two distinct bands were seen: The most prominent band at a size of approximately 300 bp and a somewhat weaker band at approximately 350 bp.

Both fragments were digested with BamHI and XhoI which cut in the overhangs introduced by the PCR primers. The digested fragments were isolated and cloned into pMT2188, an *Aspergillus* expression plasmid based on the plasmid pCaHj527 (see the examples of international patent application WO 00/70064) constructed as described in example 7 of Danish Patent application PA 2001 00088. The shorter fragment was found to contain the Plectasin encoding sequence as determined from the signal trapping experiment (see Example 1 above). The sequence of this shorter PCR fragment is shown as SEQ ID NO:5.

Similarly, the sequence of the longer PCR fragment was determined to contain the Plectasin encoding sequence and an additional 58 bp insert. It was noted that the 58 bp insert contains the consensus features of a fungal intron, and the amplification of this product is taken as evidence for incomplete intron removal in the mRNA pool and derived cDNA library. The sequence of this longer PCR fragment is shown as SEQ ID NO:6. The *Aspergillus* expression plasmid for the shorter PCR product (SEQ ID NO:5) was named pMT2548.

Example 3

Expression of Plectasin in *Aspergillus*

PMT2548 was transformed into *Aspergillus oryzae* strain BECh2 (disclosed in international patent application WO 00/39322) and into *Aspergillus niger* MBin118. 30 transformants of each strain were re-isolated twice under selective and noninducing conditions on Cove minimal plates with sucrose and acetamide. To test expression of Plectasin, transformants were grown for 6 days at 30 degrees celcius in tubes with 10 ml YPM (2% peptone, 1% yeast extract, 2% maltose). Supernatants were run on NuPage 10% Bis-Tris SDS gels (Invitrogen) as recommended by the manufacturer with MES running buffer to allow separation in the low Mw range. Both *Aspergillus* strains grew well even when induced for the expression of Plectasin. A distinct band of the size expected for Plectasin was seen in most transformants whereas this band was not seen in the untransformed host strains *A. oryzae* BECh2 and *A. niger* MBin118. It appeared that the Plectasin band was stronger in the BECh2 transformants than in the MBin118 transformants. It was estimated, very roughly and on the basis of staining intensity only, that the yield under these growth conditions was in the order of 10-50 mg per liter of culture medium.

Example 4

Cloning of Plectasin into the Suicide Expression System (SES)

The Plectasin fragment was amplified by PCR using the full length Plectasin cDNA as template (Plectasin_6_B12) and the NcoI and XbaI linker primers DR34F and DR34R.

```
DR34F:    ccggccatgg gatttggatg     (SEQ ID NO: 9)
          caatggtcct tggg DR34R:    gccgtctaga gccatctagt     (SEQ ID NO: 10)
          aacacttgca aacaaagccc
          cccttagc
```

The PCR amplification was carried out using PWO DNA polymerase according to the manufacturer (Roche Bioscience, CA). The PCR product was digested with NcoI and XbaI and directional-inserted into pHHA and pHH plasmids (disclosed in the examples of international patent application WO 00/73433). The resulting plasmids were named pDR-18-plectasin for cytoplasmic expression of the peptide and pDRS-18-plectasin for periplasmic expression.

Both plasmids contained the following amino acid sequence of the Plectasin fragment:

(SEQ ID NO: 11)
mGFGCNGPWDEDDMQCHNHCKSIKGYKGGYCAKGGFVCKCY where m (methionine) is not present in the native Plectasin but was introduced as a result of the cloning strategy.

Growth Inhibition of *E. coli* Upon Expression of Plectasin

In order to evaluate whether *E. coli* was growth inhibited in liquid media upon induction of endogenous Plectasin expression, the following experiment was conducted as disclosed in the examples of international patent application WO 00/73433. Briefly, fresh overnight cultures of cells containing either pDRS-18-plectasin, pDR-18-plectasin, pHH or pHHA plasmid were diluted 300-fold into 150 micro liter of LB or LB containing 0.1% arabinose in a microtiter plate and incubated at 37 degrees celcius with vigorous shaking. The growth curve was monitored by measuring $OD_{450}$ at regular intervals using an ELISA reader. Results showed that Plectasin inhibited 41% cell growth when directed to the periplasm however, it did not affect cell growth when expressed in the cytoplasm (see table below).

TABLE 2

| Inhibition of cell growth. | |
|---|---|
| Construct | % Inhibition |
| pHH | 16% |
| pHH-plectasin (pDRS-18-plectasin) | 41% |
| pHHA | 12% |
| pHHA-plectasin (pDR-18-plectasin) | 13% |

Example 5

Cloning, Expression and Activity Evaluation of *P. nigrella* Plectasin in *E. Coli*

Cloning of Plectasin from *P. nigrella* in pET31 b+

In order to produce Plectasin for antimicrobial activity assays, the cDNA encoding Plectasin was inserted into the expression vector pET31b+ (Novagen Inc., WI). By specifically designed oligonucleotides (Primer1 and Primer2) the Plectasin gene was amplified by polymerase chain reaction using the PWO DNA polymerase according to the manufacturer (Roche Bioscience, CA).

```
Primer1:  attattcagatgctggatcc       (SEQ ID NO: 12)
          gaaaaacctgcgtcgcatta
          tccgcaaaggcatccatatc Primer2:  aataatctcgagttattagc       (SEQ ID NO: 13)
          catatttttaatgatatgg
          atgcctttgcggataatgcg ac
```

Enzymatic digestion of flanking restriction endonuclease sites (AlwNI/AvaI) enabled us to clone this gene as a fusion construct in pET31b+ (standard procedures as described by the manufacturer (New England Biolabs Inc., MA). All standard protocols has been described elsewhere (Sambrook, Fritsch, and Maniatis, 1989).

Transformation and Expression of *P. nigrella* Plectasin in *E. coli*

Recombinant pET31b+ was transformed into *E. coli* Novablue is described by the manufacturer (Novagen). Plasmid was prepared by QIAprep Mini Columns (QIAGEN Inc., CA) and sequenced by automated sequencing using plasmid specific primers (Primer3 and Primer4).

```
Primer3:  tgctagttat tgctcagcgg      (SEQ ID NO: 14)

Primer4:  accgtagttg cgcccatcg       (SEQ ID NO: 15)
```

Plasmid was transformed in *E. coli* BLR-DE3 according to the manufacturer (Novagen). Bacteria were cultivated in LB media to $OD_{600}$~0.8 and recombinant protein synthesis was initiated by 1 mM IPTG (Isopropyl beta-D-Thiogalactopyranoside). Upon 3 hours of induction, bacteria were harvested, resuspended in 1/10 volumen buffer A (50 mM Tris-HCl, 1 mM EDTA, 100 mM NaCl, pH 8) and lysed by pressure disruption (1500 mBar). Resulting pellet was washed twice in buffer B (50 mM Tris-HCl, 10 mM EDTA, 0.5% Triton X-100, 100 mM NaCl, pH 8). All standard protocols has been described elsewhere (Sambrook, Fritsch, and Maniatis, 1989).

Purification of *P. nigrella* Plectasin from *E. coli* Inclusion Bodies

The pellet resulting from the above purification contained purified inclusion bodies. To liberate the peptide from the KSI fusion partner, acid hydrolysis was performed on an engineered Asp-Pro site, introduced N-terminally to the Plectasin encoding gene.

Inclusion bodies were resuspended in 100 mM sodium phosphate (pH 2.3) and incubated overnight at 85 degrees celcius. Resulting supernatant contained Proline-Plectasin and sample was neutralised by 100 mM sodium phosphate (pH 12.3). The identity of Proline-Plectasin was confirmed by mass-spectrometry. All standard protocols has been described elsewhere (Sambrook, Fritsch, and Maniatis, 1989).

Antimicrobial Activity by Radial Diffusion Assay

A modified version of a previously published protocol has been applied in the detection of antimicrobial activity (Lehrer et al., (1991) Ultrasensitive assays for endogenous antimicrobial polypeptides *J Immunol Methods* 137: 167-173). Target bacteria ($10^6$ colony forming units (CFU)) were added to 10 ml of underlay agarose (1% low electro-endosmosis agarose, 0.03% Trypticase soy broth, 10 mM sodium phosphat, pH 7.4, 37 degrees celcius). Suspension was solidified on an INTEGRID Petri Dish (Becton Dickinson Labware, N.J.). A 3 mm Gel Puncher was used to make holes in the underlay agarose (Amersham Pharmacia Biotech, Sweden). Samples were added to the holes and incubated at 37 degrees celcius, 3 hours. An overlay was poured on top and the plate was incubated overnight (LB media, 7.5% Agar). Antimicrobial activity was seen as bacterial clearing zones around the wells. Living cells was counterstained by adding 10 ml, 0.2 mM MTT (3-(4,5-Dimethylthiazol-2-yl)-2,5-diphenyltetrazolium bromide Thiazolyl blue). All standard protocols has been described elsewhere (Sambrook, Fritsch, and Maniatis, 1989).

Antimicrobial Activity of Plectasin Against *Bacillus subtilis*

To evaluate the anti-microbial activity of Plectasin, fermentation broths of recombinant *Aspergillus oryzae* were applied in 2-fold serial dilutions in a radial diffusion assay (described above). Large clearing zones were seen when testing the sample against *Bacillus subtilis* following the above protocol. The largest clearing zone was obtained with undiluted fermentation broth (15 mm), whereas samples taken from non-recombinant *Aspergillus oryzae* shoved no antimicrobial activity against *Bacillus subtilis*.

Plectasin Expressed Through Inclusion Bodies in an Alternative *E. Coli* Host

To increase the amount of recovered Plectasin with antimicrobial activity, Plectasin was expressed in *E. coli* Origami-DE3 (Novagen Inc.). This strain carries a mutation in the genes encoding thioredoxin reductase (trxB) and glutathione reductase (gor). The recombinant pET31 b+ plasmid encoding Plectasin was transformed in *E. coli* Origami-DE3 according to the manufacturer (Novagen). Cultivation, expression and isolation of Plectasin containing inclusion bodies was done as described above (Transformation and Expression of *P. nigrella* Plectasin in *E. coli*). Recovery of Plectasin was as described above (Purification of *P. nigrella* Plectasin from *E. coli* inclusion bodies). Subsequently, radial diffusion assay was used to access the antimicrobial activity (see above: Antimicrobial activity by Radial Diffusion Assay).

Results show that producing Plectasin peptides in *E. coli* Origami-DE3 results in a 5-10 fold increase in antimicrobial activity of the peptide. The increased biological activity of Plectasin was further supported by the fact that similar results were obtained expressing another defensin, the human beta-defensin 3. We conclude that *E. coli* strains that allow the formation of disulphide bonds in the cytoplasm is generally applicable in the biosynthesis of biologically active defensins and other disulphide bridged antimicrobial peptides.

Example 6

Construction of *Saccharomyces cerevisiae* Expression Vector for Plectasin

In order to evaluate expression of Plectasin in *S. cerevisiae*, two different plasmid constructs, pHH3875 and pHH3876, were made. pHH3875 encodes the alpha-leader from *S. cerevisiae* fused to the mature Plectasin. Plectasin can be liberated from the alpha-leader and hence matured through a KEX2 cleavage sequence. pHH3876 encodes the alpha-leader fused to the pro-region of Plectasin followed by the mature Plectasin. In this construct, one KEX2 site is present between the alpha-leader and the pro-region of Plectasin, while another KEX2 site separates the pro-region of Plectasin with Plectasin itself.

Construction of pHH3875—Alpha-Leader/KEX2/Plectasin

The Plectasin gene was amplified in a standard PCR reaction using the primers pHH3875-Forw and pHH3875-Rev described below. The *Aspergillus* plasmid pMT2548 from example 2 was used as DNA template in the PCR reaction. The resulting DNA fragment was purified using Qiaquick PCR purification kit (Qiagen) and restricted with XbaI and ClaI which cut in the overhangs introduced by the primers. The fragment was further purified from a 2% agarose gel and ligated into a *S. cerevisiae* expression vector also restricted with XbaI and ClaI. This 2µ based *E. coli*/yeast shuttle vector employs the constitutive tpi promoter to drive the expression of the alpha-leader/plectasin fusion, uses beta-lactamase for phenotypic selection in *E. coli*, and carries the POT gene for plasmid selection in the Δtpi yeast (MT663; a/α, Δtpi/Δtpi, pep4-3/pep4-3).

```
Primer pHH3875-Forw:
gaagg ggtat cgatg gctaa gagag      (SEQ ID NO: 18)
gattt ggatg caatg gtcct tggga
tgagg Primer pHH3875-Rev:
cttag tttct agact agtaa cactt      (SEQ ID NO: 19)
gcaaa caaag ccccc c
```

Construction of pHH3876—Alpha-Leader/KEX2/Pro-Region/KEX2/Plectasin

The protocol for construction of pHH3876 is identical to that of pHH3875 except for the DNA primers employed. For pHH3876, the primers described below were used:

```
Primer pHH3876-Forw:
gaagg ggtat cgatg gctaa gagag      (SEQ ID NO: 20)
caccc cagcc tgttc ccgag gctta
cgc Primer pHH3876-Rev (identical to
pHH3875-Rev):
cttag tttct agact agtaa cactt      (SEQ ID NO: 21)
gcaaa caaag ccccc c
```

Expression of Plectasin in *S. cerevisiae*

The plasmids pHH3902 (control), pHH3875 and pHH3876 were transformed into the *S. cerevisiae* strain MT633 using a lithium acetate protocol. Several transformants of pHH3902, pHH3875 and pHH3876 were selected, streaked on SC ground/agar (containing SC ground agar, 2% D-glucose, 0.02% threonin) plates and incubated at 30 degrees Celsius until colonies developed.

To test expression, individual colonies were inoculated in 10 ml of liquid SC ground (containing SC ground, 2% D-glucose, 0.02% threonin), incubated under vigorous shaking at 30 degrees Celsius for 3 days. Supernatants were run on 16% Tricine gels (Novex) to give optimal separation in the low molecular weight area. In parallel, supernatants were concentrated from 500 microliter to 20 microliter using a microcon spin column with a MW cut-off of 3 kDa. All samples from pHH3875 and pHH3876 showed peptide bands of the expected size. The concentrated samples showed the most prominent bands.

In order to obtain more detailed information, the supernatants were analyzed using a MALDI-type mass spectrometer (Voyager DE-Pro from Perspective Biosystems).

For pHH3875, a major peak was observed at masses 4410-4411. This is very close to the expected mass of 4402 for correctly produced and processed Plectasin.

For pHH3876, several peaks were observed. The two most prominent peaks were found at masses 4411-4413 and 7870-7871. The 4411 peak again is in agreement with correctly processed plectasin. The peak at 7870 corresponds best to semi-processed Plectasin where the Pro-region is not cleaved from the Plectasin. Several breakdown products of presumably the 7870 peak were observed.

Activity of Plectasin from pHH3875 and pHH3876

The supernatants described above were analyzed in a radial diffusion assay as described in Example 5.

TABLE 3

| Plasmid | Approximate zone of inhibition (mm). | |
|---------|--------|--------------|
|         | Normal | Concentrated |
| pHH3902 | 0      | 0            |
| pHH3875 | 5      | 12           |
| pHH3876 | 8      | 14           |

Surprisingly, pHH3876 yielded the largest inhibition zone indicating more product or product of higher activity as compared to pHH3875.

HTP Screening of Plectasin Variants

In order to further optimize the antimicrobial activity of Plectasin, a high throughput (HTP) assay for activity is desired. To set up such a system, yeast cells containing the control plasmid, pHH3902, or the two Plectasin expression plasmids, pHH3875 and pHH3876, were grown up in 96 well microtiter plates. At a reasonable cell density, either 5 or 20 microliter of the yeast culture were removed from the microtiter plate and used in a radial diffusion assay as described in Example 5. Again, clearing zones on the radial diffusion test plate were evident from the supernatants originating from the two Plectasin-producing strains, pHH3875 and pHH3876. As observed above, the clearing zones were larger for the supernatants originating from pHH3876. No clearing zones were observed from the control plasmid. This indicates that this simple HTP assay can discriminate between yeast cells expressing different levels of antimicrobial activities, and is feasible for screening Plectasin variants with desired activities.

Example 7

Construction of Inducible Yeast Production and HTP Screening System for Plectasin Construction of pYES2-3902, pHH3886 (Plectasin) and pHH3887 (Pro-Plectasin)

In order to evaluate inducible expression systems and the potential for setting up a HTP screening system for identifying Plectasin variants with improved bioactivity, inducible expression vectors encoding Plectasin and pro-plectasin were constructed using pYES2.

pYES2 (Invitrogen) is a 5.9 kb vector designed for inducible expression of recombinant proteins and peptides in *Saccharomyces cerevisiae*. The vector contains features such as a yeast GAL1 promoter for high-level inducible expression by galactose and repression by glucose. Uracil prototrophy and ampicillin resistance are employed for selection of transformants in the yeast and *E. coli* cell, respectively.

Three plasmids were constructed; a control plasmid, pYES-3902, and two plasmids encoding Plectasin, pHH3886 and pHH3887.

As pYES2 is a non-fusion vector, the entire alpha-leader regions from pHH3902, pHH3875 and pHH3876 were PCR amplified in a standard PCR reaction. The fragments were run on a 2% agarose gel, purified using Qiagen purification kit, and restricted with HindIII and XbaI, and ligated into the corresponding sites in the plasmid pYES2. This positions the alpha-leader in front of the GAL1 promoter. The ligation mix was transformed into competent *E. coli*. Transformants were re-streaked and a number of individual clones analyzed for plasmids with insert of the correct size. Final verification was done by DNA sequencing using the primers AOP107 and AOP446. The plasmids are designated pYES2-3902 (control), pHH3886 (Plectasin) and pHH3887 (Pro-plectasin).

```
Primer    caata taaaa aagct agctt   (SEQ ID NO: 22)
AOP107:   tccg

Primer    ccggc tgaag ctgct atcgg   (SEQ ID NO: 23)
AOP446:
```

The three plasmids, pYES-3902, pHH3886 and pHH3887 were transformed into yeast strain JG169, and plated on glucose (0.5%)/galactose (1.5%) containing plates. The glucose ensures formation of colonies of a suitable size and after depletion of the glucose, galactose ensures further growth, induction of transcription and corresponding production of Plectasin. After colonies had formed, a lawn (approx. $10^6$ cfu) of an indicator strain, *B. subtilis*, was overlaid the colonies and the plates further incubated overnight. As seen with the other yeast plasmids described above, the yeast strain harboring the control plasmid did not result in a clearing zone, whereas pHH3886 and pHH3887 both gave rise to clearing zones. The largest clearing zones were observed with pHH3887 encoding Pro-plectasin.

Example 8

Construction of Inducible Yeast Production and HTP Screening System for Plectasin Construction of Mutated Plectasin Libraries Mutated Plectasin libraries were constructed using error prone PCR. Randomly mutated DNA fragments were generated using the primers pYES-mut and pHH3885-Rev and either the template pHH3875 (Pro-plectasin) or pHH3876 (Plectasin) in a PCR reaction containing 0.5 mM $MnCl_2$.

```
Primer pYES-mut:
taaatactac tattgccagc attgctgcta  (SEQ ID NO: 24)
aagaagaagg ggtatcgatg gccaagaga Primer pHH3885-Rev:
tgtaagcgtg acataactaa ttacatgatg  (SEQ ID NO: 25)
cggccctcta ga
```

The fragments were run on a 2% agarose gel, purified using Qiagen purification kit and inserted into the plasmid pYES2-3902. The plasmids were electroporated into competent yeast cells JG169.

The two different libraries were plated on large agar plates (23 cm×23 cm) containing 0.5% glucose and 1.5% galactose. After incubation at 30 degrees Celsius for 2 days, the library plates were overlaid with a thin agarose layer containing approx. $10^7$ cfu of *B. subtilis*. The plates were incubated further for 24 hours at 30 degrees Celsius. Approximately 10,000 colonies were tested. Yeast colonies giving rise to significant clearing zones were isolated for further characterization.

Deposit of Biological Material

The following biological material has been deposited under the terms of the Budapest Treaty with the Centraalbureau Voor Schimmelcultures (CBS), Uppsalalaan 8, 3584 CT Utrecht, The Netherlands (alternatively P.O. Box 85167, 3508 AD Utrecht, The Netherlands), and given the following accession number:

| Deposit | Accession Number | Date of Deposit |
| --- | --- | --- |
| *Pseudoplectania nigrella* | CBS 444.97 | 28 Jan. 1997 |

The deposit was made by Novo Nordisk A/S, and was later assigned to Novozymes A/S.

Classification of *Pseudoplectania nigrella*:

Eukaryota; Fungi; Ascomycota; Pezizomycotina; Pezizomycetes; Pezizales; Sarcosomataceae; Pseudoplectania.

The invention claimed is:

1. An isolated polypeptide having antimicrobial activity, which has at least 80% sequence identity with amino acids 1 to 40 of SEQ ID NO: 2.

2. The polypeptide of claim 1, which has at least 85% sequence identity with amino acids 1 to 40 of SEQ ID NO: 2.

3. The polypeptide of claim 1, which has at least 90% sequence identity with amino acids 1 to 40 of SEQ ID NO: 2.

4. The polypeptide of claim 1 which has at least 95% sequence identity with amino acids 1 to 40 of SEQ ID NO: 2.

5. The polypeptide of claim 1, which has at least 99% sequence identity with amino acids 1 to 40 of SEQ ID NO: 2.

6. The polypeptide of claim 1, which comprises the amino acids 1 to 40 of SEQ ID NO: 2.

7. The polypeptide of claim 1, which consists of the amino acids 1 to 40 of SEQ ID NO: 2.

8. An antimicrobial composition comprising the polypeptide of claim 1.

9. The composition of claim 8, which further comprises an additional biocidal agent.

10. A detergent composition comprising a surfactant and the polypeptide of claim 1.

11. An animal feed additive comprising
(a) at least one polypeptide of claim 1; and
(b) at least one fat soluble vitamin, and/or
(c) at least one water soluble vitamin, and/or
(d) at least one trace mineral, and/or
(e) at least one macro mineral.

12. The animal feed additive of claim 11, which further comprises phytase, xylanase, galactanase, and/or beta-glucanase.

13. An animal feed composition having a crude protein content of 50 to 800 g/kg and comprising at least one polypeptide of claim 1.

14. A method for killing or inhibiting growth of microbial cells comprising contacting the microbial cells with the polypeptide of claim 1.

15. A method of treating a microbial infection, comprising administering to a human or animal the polypeptide of claim 1 in an amount effective to treat the microbial infection.

* * * * *

UNITED STATES PATENT AND TRADEMARK OFFICE
CERTIFICATE OF CORRECTION

PATENT NO. : 7,972,814 B2
APPLICATION NO. : 10/496229
DATED : July 5, 2011
INVENTOR(S) : Schnorr et al.

It is certified that error appears in the above-identified patent and that said Letters Patent is hereby corrected as shown below:

On the Title page of the patent, in section (73), correct the name of the assignee as follows Delete "Novozymes Adenivro Biotech A/S" and insert --Novozymes Adenium Biotech A/S--.

Signed and Sealed this
Eleventh Day of October, 2011

David J. Kappos
*Director of the United States Patent and Trademark Office*

SEQUENCE LISTING

```
<160> NUMBER OF SEQ ID NOS: 17

<210> SEQ ID NO 1
<211> LENGTH: 288
<212> TYPE: DNA
<213> ORGANISM: Pseudoplectania nigrella
<220> FEATURE:
<221> NAME/KEY: CDS
<222> LOCATION: (1)..(285)
<220> FEATURE:
<221> NAME/KEY: sig_peptide
<222> LOCATION: (1)..(69)
<220> FEATURE:
<221> NAME/KEY: mat_peptide
<222> LOCATION: (166)..()

<400> SEQUENCE: 1
```

```
atg caa ttt acc acc atc ctc tcc atc ggt atc acc gtc ttc gga ctt    48
Met Gln Phe Thr Thr Ile Leu Ser Ile Gly Ile Thr Val Phe Gly Leu
-55             -50                 -45                 -40 ctc aac acc gga gcc ttt gca gca ccc cag cct gtt ccc gag gct tac    96
Leu Asn Thr Gly Ala Phe Ala Ala Pro Gln Pro Val Pro Glu Ala Tyr
                -35                 -30                 -25 gct gtt tct gat ccc gag gct cat cct gac gat ttt gct ggt atg gat   144
Ala Val Ser Asp Pro Glu Ala His Pro Asp Asp Phe Ala Gly Met Asp
            -20                 -15                 -10 gcg aac caa ctt cag aaa cgt gga ttt gga tgc aat ggt cct tgg gat   192
Ala Asn Gln Leu Gln Lys Arg Gly Phe Gly Cys Asn Gly Pro Trp Asp
        -5              -1  1               5 gag gat gat atg cag tgc cac aat cac tgc aag tct att aag ggt tac   240
Glu Asp Asp Met Gln Cys His Asn His Cys Lys Ser Ile Lys Gly Tyr
10              15                  20                  25 aag gga ggt tat tgt gct aag ggg ggc ttt gtt tgc aag tgt tac tag   288
Lys Gly Gly Tyr Cys Ala Lys Gly Gly Phe Val Cys Lys Cys Tyr
                30                  35                  40

<210> SEQ ID NO 2
<211> LENGTH: 95
<212> TYPE: PRT
<213> ORGANISM: Pseudoplectania nigrella

<400> SEQUENCE: 2

Met Gln Phe Thr Thr Ile Leu Ser Ile Gly Ile Thr Val Phe Gly Leu
-55             -50                 -45                 -40

Leu Asn Thr Gly Ala Phe Ala Ala Pro Gln Pro Val Pro Glu Ala Tyr
                -35                 -30                 -25

Ala Val Ser Asp Pro Glu Ala His Pro Asp Asp Phe Ala Gly Met Asp
            -20                 -15                 -10

Ala Asn Gln Leu Gln Lys Arg Gly Phe Gly Cys Asn Gly Pro Trp Asp
        -5              -1  1               5

Glu Asp Asp Met Gln Cys His Asn His Cys Lys Ser Ile Lys Gly Tyr
10              15                  20                  25

Lys Gly Gly Tyr Cys Ala Lys Gly Gly Phe Val Cys Lys Cys Tyr
                30                  35                  40

<210> SEQ ID NO 3
<211> LENGTH: 95
<212> TYPE: PRT
<213> ORGANISM: Pseudoplectania nigrella
<220> FEATURE:
<221> NAME/KEY: SIGNAL
<222> LOCATION: (1)..(23)
<220> FEATURE:
<221> NAME/KEY: PROPEP
<222> LOCATION: (24)..(55)
<220> FEATURE:
<221> NAME/KEY: PEPTIDE
<222> LOCATION: (56)..(95)

<400> SEQUENCE: 3

Met Gln Phe Thr Thr Ile Leu Ser Ile Gly Ile Thr Val Phe Gly Leu
1               5                   10                  15

Leu Asn Thr Gly Ala Phe Ala Ala Pro Gln Pro Val Pro Glu Ala Tyr
                20                  25                  30

Ala Val Ser Asp Pro Glu Ala His Pro Asp Asp Phe Ala Gly Met Asp
            35                  40                  45

Ala Asn Gln Leu Gln Lys Arg Gly Phe Gly Cys Asn Gly Pro Trp Asp
        50                  55                  60

Glu Asp Asp Met Gln Cys His Asn His Cys Lys Ser Ile Lys Gly Tyr
```

| 65 | | | 70 | | | 75 | | | 80 | | |
|---|---|---|---|---|---|---|---|---|---|---|---|
| Lys | Gly | Gly | Tyr | Cys | Ala | Lys | Gly | Gly | Phe | Val | Cys |
| | | | 85 | | | | | 90 | | | |

| Lys | Cys | Tyr |
|---|---|---|
| | 95 | |

<210> SEQ ID NO 4
<211> LENGTH: 2403
<212> TYPE: DNA
<213> ORGANISM: Artificial Sequence
<220> FEATURE:
<223> OTHER INFORMATION: Vector pMHas5

<400> SEQUENCE: 4

```
cgataagcta gcttcacgct gccgcaagca ctcagggcgc aagggctgct aaaggaagcg      60
gaacacgtag aaagccagtc cgcagaaacg gtgctgaccc cggatgaatg tcagctactg     120
ggctatctgg acaagggaaa acgcaagcgc aaagagaaag caggtagctt gcagtgggct     180
tacatggcga tagctagact gggcggtttt atggacagca agcgaaccgg aattgccagc     240
tggggcgccc tctggtaagg ttgggaagcc ctgcaaagta aactggatgg ctttcttgcc     300
gccaaggatc tgatggcgca ggggatcaag atctgatcaa gagacaggat gaggatcgtt     360
tcgcatgatt gaacaagatg gattgcacgc aggttctccg ccgcttgggt ggagaggct      420
attcggctat gactgggcac aacagacaat cggctgctct gatgccgccg tgttccggct     480
gtcagcgcag gggcgcccgg ttcttttgt caagaccgac ctgtccggtg ccctgaatga     540
actccaagac gaggcagcgc ggctatcgtg gctggccacg acgggcgttc cttgcgcagc     600
tgtgctcgac gttgtcactg aagcgggaag gactggctg ctattgggcg aagtgccggg      660
gcaggatctc ctgtcatctc accttgctcc tgccgagaaa gtatccatca tggctgatgc     720
aatgcggcgg ctgcatacgc ttgatccggc tacctgccca ttcgaccacc aagcgaaaca     780
tcgcatcgag cgagcacgta ctcggatgga agccggtctt gtcgatcagg atgatctgga     840
cgaagagcat caggggctcg cgccagccga actgttcgcc aggctcaagg cgcggatgcc     900
cgacggcgag gatctcgtcg tgacccatgg cgatgcctgc ttgccgaata tcatggtgga     960
aaatggccgc ttttctggat tcatcgactg tggccggctg ggtgtggcgg accgctatca    1020
ggacatagcg ttggctaccc gtgatattgc tgaagagctt ggcggcgaat gggctgaccg    1080
cttcctcgtg ctttacggta tcgccgctcc cgattcgcag cgcatcgcct tctatcgcct    1140
tcttgacgag ttcttctgag cgggactctg gggttcgcga tgataagctg tcaaacatga    1200
gaattacaac ttatatcgta tggggctgac ttcaggtgct acatttgaag agataaattg    1260
cactgaaatc tagaaatatt ttatctgatt aataagatga tcttcttgag atcgttttgg    1320
tctgcgcgta atctcttgct ctgaaaacga aaaaaccgcc ttgcagggcg ttttttcgaa    1380
ggttctctga gctaccaact ctttgaaccg aggtaactgg cttggaggag cgcagtcacc    1440
aaaacttgtc ctttcagttt agccttaacc ggcgcatgac ttcaagacta actcctctaa    1500
atcaattacc agtggctgct gccagtggtg cttttgcatg tctttccggg ttggactcaa    1560
gacgatagtt accggataag gcgcagcggt cggactgaac ggggggttcg tgcatacagt    1620
ccagcttgga gcgaactgcc tacccggaac tgagtgtcag gcgtggaatg agacaaacgc    1680
ggccataaca gcggaatgac accggtaaac cgaaaggcag aacaggagag cgcacgagg     1740
gagccgccag gggaaacgcc tggtatcttt atagtcctgt cgggtttcgc caccactgat    1800
ttgagcgtca gatttcgtga tgcttgtcag ggggcggag cctatggaaa aacggctttg      1860
ccttctttcc tgcgttatcc cctgattctg tggataaccg tattaccgcc tttgagtgag    1920
ctgataccgc tcgccgcagc cgaacgaccg agcgcagcga gtcagtgagc gaggaagcgg    1980
```

```
aagagcgccc aatacgcaaa ccgcctctcc ccgcgcgttg gccgattcat taatgcagct   2040
ggcacgacag gtttcccgac tggaaagcgg gcagtgagcg caacgcaatt aatgtgagtt   2100
agctcactca ttaggcaccc caggctttac actttatgct tccggctcgt atgttgtgtg   2160
gaattgtgag cggataacaa tttcacacag gaattcacag ctatgctaga gcggccgctc   2220
gacctgcagg catgcaagct tggcactggc cgtcgtttta caacgtcgtg actgggaaaa   2280
ccctggcgtt acccaactta atcgccttgc agcacatccc cctttcgcca gctggcgtaa   2340
tagcgaagag gcccgcaccg atcgcccttc ccaacagttg cgcagcctga atggcgaatg   2400
gcg                                                                2403

<210> SEQ ID NO 5
<211> LENGTH: 303
<212> TYPE: DNA
<213> ORGANISM: Pseudoplectania nigrella

<400> SEQUENCE: 5
ggatccacca tgcaatttac caccatcctc tccatcggta tcaccgtctt cggacttctc     60
aacaccggag cctttgcagc accccagcct gttcccgagg cttacgctgt ttctgatccc    120
gaggctcatc ctgacgattt tgctggtatg gatgcgaacc aacttcagaa acgtggattt    180
ggatgcaatg gtccttggga tgaggatgat atgcagtgcc acaatcactg caagtctatt    240
aagggttaca agggaggtta ttgtgctaag gggggctttg tttgcaagtg ttactagctc    300
gag                                                                 303

<210> SEQ ID NO 6
<211> LENGTH: 361
<212> TYPE: DNA
<213> ORGANISM: Pseudoplectania nigrella

<400> SEQUENCE: 6
ggatccacca tgcaatttac caccatcctc tccatcggta tcaccgtctt cggacttctc     60
aacaccggag cctttgcagc accccagcct gttcccgagg cttacgctgt ttctgatccc    120
gaggctcatc ctgacgattt tgctggtatg gatgcgaacc aacttcagaa acgtggattt    180
ggatgcaatg gtccttggga tgaggatgat atgcagtgcc acaagtaaga atcacttata    240
actatagatt aagccaagag tattggaact gatgataaat agtcactgca agtctattaa    300
gggttacaag ggaggttatt gtgctaaggg gggctttgtt tgcaagtgtt actagctcga    360
g                                                                   361

<210> SEQ ID NO 7
<211> LENGTH: 35
<212> TYPE: DNA
<213> ORGANISM: Artificial Sequence
<220> FEATURE:
<223> OTHER INFORMATION: Primer 178

<400> SEQUENCE: 7
tctggatcca ccatgcaatt taccaccatc ctctc                               35

<210> SEQ ID NO 8
<211> LENGTH: 32
<212> TYPE: DNA
<213> ORGANISM: Artificial Sequence
<220> FEATURE:
<223> OTHER INFORMATION: Primer 179

<400> SEQUENCE: 8
```

```
tctctcgagc tagtaacact tgcaaacaaa gc                                    32
```

<210> SEQ ID NO 9
<211> LENGTH: 34
<212> TYPE: DNA
<213> ORGANISM: Artificial Sequence
<220> FEATURE:
<223> OTHER INFORMATION: Primer DR34F

<400> SEQUENCE: 9

```
ccggccatgg gatttggatg caatggtcct tggg                                  34
```

<210> SEQ ID NO 10
<211> LENGTH: 48
<212> TYPE: DNA
<213> ORGANISM: Artificial Sequence
<220> FEATURE:
<223> OTHER INFORMATION: Primer DR34R

<400> SEQUENCE: 10

```
gccgtctaga gccatctagt aacacttgca aacaaagccc cccttagc                   48
```

<210> SEQ ID NO 11
<211> LENGTH: 41
<212> TYPE: PRT
<213> ORGANISM: Artificial Sequence
<220> FEATURE:
<223> OTHER INFORMATION: met-Plectasin

<400> SEQUENCE: 11

```
Met Gly Phe Gly Cys Asn Gly Pro Trp Asp Glu Asp Asp Met Gln Cys
1               5                   10                  15

His Asn His Cys Lys Ser Ile Lys Gly Tyr Lys Gly Gly Tyr Cys Ala
            20                  25                  30

Lys Gly Gly Phe Val Cys Lys Cys Tyr
        35                  40
```

<210> SEQ ID NO 12
<211> LENGTH: 60
<212> TYPE: DNA
<213> ORGANISM: Artificial Sequence
<220> FEATURE:
<223> OTHER INFORMATION: Primer1

<400> SEQUENCE: 12

```
attattcaga tgctggatcc gaaaaacctg cgtcgcatta tccgcaaagg catccatatc     60
```

<210> SEQ ID NO 13
<211> LENGTH: 62
<212> TYPE: DNA
<213> ORGANISM: Artificial Sequence
<220> FEATURE:
<223> OTHER INFORMATION: Primer2

<400> SEQUENCE: 13

```
aataatctcg agttattagc catattttt aatgatatgg atgcctttgc ggataatgcg     60
ac                                                                    62
```

<210> SEQ ID NO 14
<211> LENGTH: 20
<212> TYPE: DNA
<213> ORGANISM: Artificial Sequence
<220> FEATURE:
<223> OTHER INFORMATION: Primer3

```
<400> SEQUENCE: 14
tgctagttat tgctcagcgg                                                  20

<210> SEQ ID NO 15
<211> LENGTH: 19
<212> TYPE: DNA
<213> ORGANISM: Artificial Sequence
<220> FEATURE:
<223> OTHER INFORMATION: Primer4

<400> SEQUENCE: 15
accgtagttg cgcccatcg                                                   19

<210> SEQ ID NO 16
<211> LENGTH: 20
<212> TYPE: DNA
<213> ORGANISM: Artificial sequence
<220> FEATURE:
<223> OTHER INFORMATION: Primer A

<400> SEQUENCE: 16
agcgtttgcg gccgcgatcc                                                  20

<210> SEQ ID NO 17
<211> LENGTH: 21
<212> TYPE: DNA
<213> ORGANISM: Artificial sequence
<220> FEATURE:
<223> OTHER INFORMATION: Primer B

<400> SEQUENCE: 17
ttattcggtc gaaaaggatc c                                                21
```